United States Patent [19]

Nakamura et al.

[11] Patent Number: 4,660,946
[45] Date of Patent: Apr. 28, 1987

[54] CORNEA SHAPE MEASURING METHOD AND APPARATUS

[75] Inventors: Yukitugu Nakamura, Sagamihara; Takashi Masuda, Kawasaki; Kyoji Sekiguchi, Tokyo, all of Japan

[73] Assignee: Canon Kabushiki Kaisha, Tokyo, Japan

[21] Appl. No.: 734,234

[22] Filed: May 14, 1985

Related U.S. Application Data

[63] Continuation of Ser. No. 416,355, Sep. 8, 1982, abandoned.

[30] Foreign Application Priority Data

Sep. 21, 1981 [JP] Japan ............................ 56-149058
Sep. 25, 1981 [JP] Japan ............................ 56-151662

[51] Int. Cl.⁴ ............................................ A61B 3/10
[52] U.S. Cl. .................................... 351/212; 351/247
[58] Field of Search ............... 351/211, 212, 221, 208, 351/206, 247

[56] References Cited

U.S. PATENT DOCUMENTS

| | | |
|---|---|---|
| 1,750,931 | 3/1930 | Kellner et al. |
| 3,932,030 | 1/1976 | Hasegawa et al. ............... 351/206 |
| 3,969,019 | 7/1976 | Nohda ............................ 351/212 |
| 4,312,574 | 1/1982 | Wilms ............................ 351/212 |
| 4,439,025 | 3/1984 | Smirmaul ....................... 351/212 |
| 4,569,576 | 2/1986 | Karpov et al. .................. 351/212 |

*Primary Examiner*—Rodney B. Bovernick
*Assistant Examiner*—P. M. Dziercynski
*Attorney, Agent, or Firm*—Fitzpatrick, Cella, Harper & Scinto

[57] ABSTRACT

A method and apparatus in which a predetermined index is projected onto the cornea of an eye to be examined and the shape of the cornea determining the refractive power, the degree of astigmatism, the direction of astigmatic axis, etc. of the cornea is measured from the general elliptical shape of the image of the index reflected by the cornea. Independently of the center of the ellipse, arbitrary position coordinates of at least five points of the image reflected by the cornea are detected, whereby the elliptical shape is calculated without enhancing the alignment accuracy in a plane perpendicular to the optical axis. The image reflected by the cornea may be electrically detected by position detects such as CCDs, whereby automation of the measurement is provided, coupled with the later signal processing. A strobo light is used for the projection of the index. Further, the shape of the cornea is obtained so that no measurement error may occur depending on a variation in operating distance, that is, without enhancing the positional accuracy in the direction of the optical axis.

20 Claims, 20 Drawing Figures

CORNEA SHAPE MEASURING METHOD AND APPARATUS

This application is a continuation of application Ser. No. 416,355 filed Sept. 8, 1982, now abandoned.

BACKGROUND OF THE INVENTION

1. Field of the Invention

Cornea shape measurement is generally carried out to obtain the refractive power, the degree of astigmatism and the direction of the astigmatic axis of the cornea and is also used for the inspection of the base curve of contact lenses.

2. Description of the Prior Art

Heretofore, in the ophthalmometer or keratometer known from U.S. Pat. No. 1,750,931 and U.S. Pat. No. 3,932,030, an index has been projected onto the cornea of an eye to be examined, the size of the reflected image thereof from the cornea has been observed by the use of a microscope, and optical member such as a prism or the like has been moved and the refractive power, etc. of the cornea have been obtained from the amount of movement of the optical member.

However, this method has utilized observation by the eye and has therefore required much time to make the measurement. These factors have, in turn, led to a problem that an error can result from movement of the eye to be examined.

Now, generally, a cornea does not have a uniform curvature in the direction of each diametral line. Therefore, the image reflected by the cornea assumes an elliptical shape and to specify this ellipse, it is known to obtain the refractive power, etc. of the cornea by measuring the maximum values in the directions of three diametral lines. This operation utilizes the fact that when the central portion of the cornea is regarded as a toric surface, the variations of the curvature of the cornea in the directions of diametral lines can be regarded as being sine-wave-like. However, in the measurement in the directions of three diametral lines, it has been necessary to enhance the alignment accuracy in a plane perpendicular to the optical axis, namely, to make the measurement optical axis and the optical axis of the eye to be examined substantially coincident with each other. That is, it has been necessary to specify the center of the ellipse and thus, measurement has generally been difficult.

SUMMARY OF THE INVENTION

It is an object of the present invention to provide a novel measuring method and apparatus which are capable of measuring the shape of a cornea without enhancing the alignment accuracy in a plane perpendicular to the optical axis.

It is a further object of the present invention to provide a measuring method and apparatus which are capable of automatically detecting the shape of a cornea and thereby measuring the shape of the cornea within a short time.

It is still a further object of the present invention to provide a measuring method and apparatus in which measurement is accurately carried out even if there is a deviation of the operating distance in the direction of the optical axis from an ideal value.

These objects are achieved by projecting the light beam from the image reflected by the cornea onto position detecting means, for example, at least three one-dimensional position detecting means, by an imaging optical system, and using the electrical signals from the position detecting means to automatically detect any arbitrary position coordinates of at least five points of the image reflected by the cornea. Further, such objects are achieved by projecting the index onto the eye to be examined from infinity and making the imaging optical system into a telecentric system.

The invention will become more fully apparent from the following detailed description thereof taken in conjunction with the accompanying drawings.

BRIEF DESCRIPTION OF THE DRAWINGS

FIG. 10 illustrates how FIGS. 10A and 10B are assembled to form a block diagram of a signal processing system.

DESCRIPTION OF THE PREFERRED EMBODIMENTS

Figure 1:
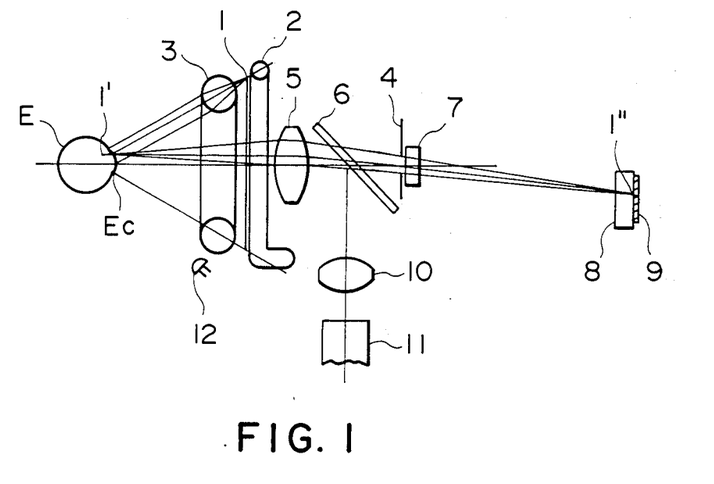
FIG. 1 and 2 are a longitudinal cross-sectional view and a transverse cross-sectional view, respectively, of a first embodiment of the apparatus according to the present invention.
Figure 2:
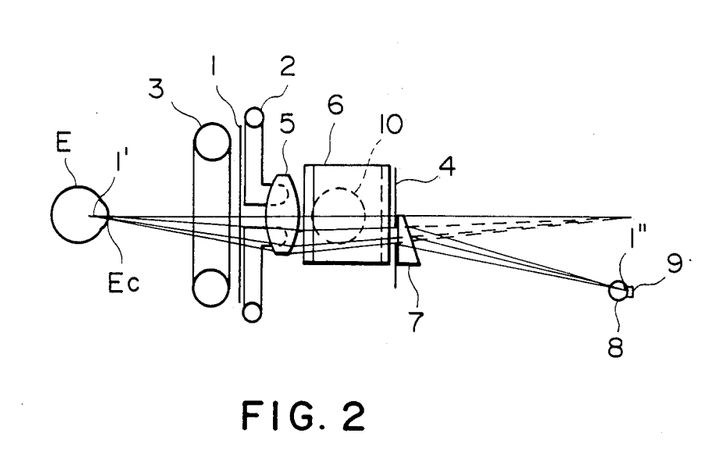

Referring to FIGS. 1 and 2, reference numeral 1 designates a ring-like slit which is an index. The ring-like slit 1 has openings narrow in the directions of diametral lines, and is illuminated by a ring-like strobo 2. The ring-like strobo 2 has a circumferential light-emitting portion with the measurement optical axis as the center. The index may be a plurality of indices arranged on the circumference. Designated by 3 is a doughnut-shaped collimating lens. The collimating lens 3 has a refractive power in a cross section in the direction of any diametral line and does not have a refractive power in a direction perpendicular to the direction of the diametral line, namely, a circumferential direction. That is, the collimating lens 3 is cylindrical. It will suffice if the lens 3 is of the above-described shape only in the effective light beam portion.

The ring-like slit 1 is disposed at a distance of the focal length of the collimating lens 3 from this lens. By this positioning, the light from the collimating lens 3 is converted into a parallel light in the cross section in the direction of the diametral line and illuminates the cornea Ec of an eye to be examined from infinity. Since the eye to be examined is thus illuminated by the light beam from infinity, the size of the image 1' reflected by the cornea does not change even when the distance between the projection index and the cornea Ec deviates somewhat from an optimum distance. The projection index may be other than the ring-like slit.

Figure 3:
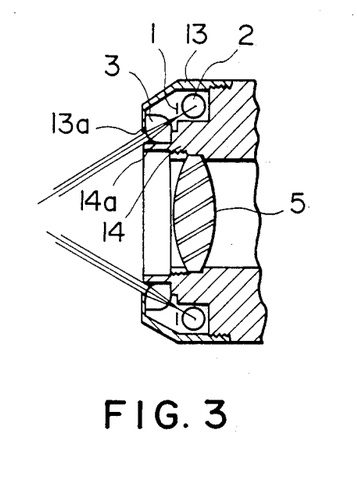
FIG. 3 is a detailed view of a part of the apparatus of FIGS. 1 and 2 for illustrating an index projection system incorporated in a lens berrel.

The reflected light from the cornea Ec is reflected toward a projection lens 5 as if it were emitted from the reflected image 1', and the light beam passing through the projection lens 5 is imaged as 1" on the detecting surface of a one-dimensional image sensor 9 (hereinafter referred to as the sensor) through a diaphragm plate 4. As shown in FIG. 3, the index projection system and the projection lens 5 may be integrally incorporated in a lens barrel.

Figure 4A:
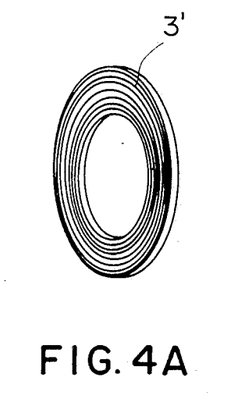
FIGS. 4A and 4B illustrate a modification using a disc-shaped Fresnel type cylindrical lens as the index projection lens.
Figure 4B:
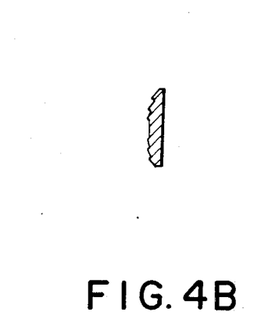

That is, the collimating lens 3 which is an annular cylindrical lens is fitted onto the outer periphery of the barrel 14 of the projection lens 5 and fixed thereto by being held down by a cover ring 13. An apeture stop may be formed by the forward outer edge 14a of the lens barrel 14 and the forward inner edge 13a of the cover ring 13. The collimating lens 3 is not restricted to the above-described cylindrical lens, but may be a disc-like Fresnel type cylindrical lens 3' as shown in FIGS. 4A and 4B. FIG. 4B shows a cross section in the direction of a diametral line of this Fresnel type cylindrical lens. This lens is one which is Fresnel-like in the direction of each diametral line, and does not have a refractive power in the circumferential direction orthogonal thereto. Such Fresnel lens can be easily mass-produced by injection molding of acrylic resin or the like.

Figure 5:
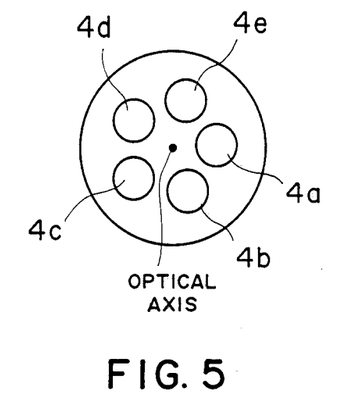
FIG. 5 shows a diaphragm plate.
Figure 6:
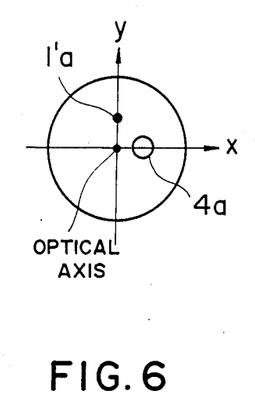
FIG. 6 illustrates a one-direction telecentric optical system.

Now, the diaphragm plate 4 provided in the optical path for projecting the image 1' by the cornea onto the one-dimensional image sensor 9 has five circular openings 4a to 4e displaced from the optical axis as shown in FIG. 5, and is disposed at a position whereat the light beam can be separated into five light beams near the focus position of the projection lens 5 in the direction of the optical axis. The light beams passing through the five circular openings are directed to five sensors 9 by a wedge prism 7 as will later be described in detail. It should be noted that, as shown in FIG. 6, each measurement diametral line direction (y direction) from the optical axis and a corresponding opening center direction (x direction) are orthogonal to each other as viewed from the direction of the optical axis. That is, the optical system constitutes a telecentric system in the measurement diametral line direction. Thus, in each measurement diametral line direction, the light rays passing through the centers of the circular openings become light rays reflected from the cornea Ec so as to be parallel to the optical axis. The reason why the stop aperture is not provided on the optical axis is that the light beams to be deflected to the respective sensors are separated, and since the center of each opening is displaced from the optical axis, the optical system is telecentric only in one direction, i.e., the y direction, and is non-telecentric in the x direction orthogonal thereto. The one-direction telecentric system is useful in the sense that any magnification error in the y direction is eliminated during the measurement in the y direction. That is, due to the above-described five openings, the optical system becomes telecentric in the direction of each corresponding diametral line. Even if the distance with respect to the eye to be examined (operating distance) deviates somewhat from an optimum value, the size of the image does not change although there occurs blurring of the image, and thus there occurs no measurement error. The wedge prism 7 is for deflecting the light beam passing through each opening of the diaphragm plate 4 to each corresponding one-dimensional image sensor 9 and, by passing through this wedge prism 7, the projected image 1" of the reflected image 1' of the cornea by the projection lens 5 is separated into five images.

The wedge prism 7 is so disposed that the direction in which the light beam is deflected is perpendicular to the detection direction of the sensor 9 as shown in FIG. 2. This is for the purposes of minimizing the sensor 9 and making the optical system into a telecentric optical system in the cross section in the direction of the diametral line containing the measurement point, as already described.

Figure 7:
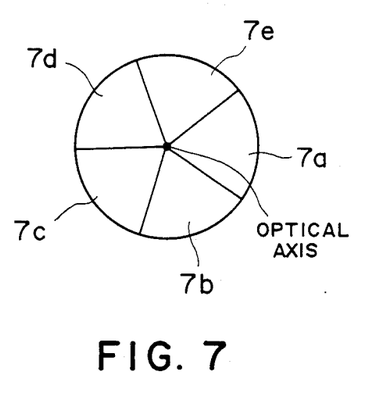
FIG. 7 illustrates a prism.

The wedge prism 7, as shown in FIG. 7, comprises five prisms 7a to 7e radially cemented together so that the peripheral portion thereof may be thick.

In FIG. 1, reference numeral 8 designates a pillar lens for imaging the openings of the diaphragm plate 4 on the detecting surfaces of sensors 9a-9e and, by this pillar lens, the light around the cornea can be condensed on the sensors 9 to enable information to be obtained even if a part of the image 1' reflected by the cornea is hidden by an eyelash or the like. This pillar lens 8 does not have a refractive power in the detection direction of the sensors but has a refractive power in a direction perpendicular thereto, and five such pillar lenses are provided each in parallel to the detection direction of one sensor correspondingly to the sensors 9a-9e. The light beam entering the sensors 9 is condensed in a direction perpendicular to the detection direction of the sensors by the pillar lenses 8.

As the sensors, use may be made of not only image sensing elements such as MOSs or CCDs but also position detecting elements such as position detectors.

Figure 8A:
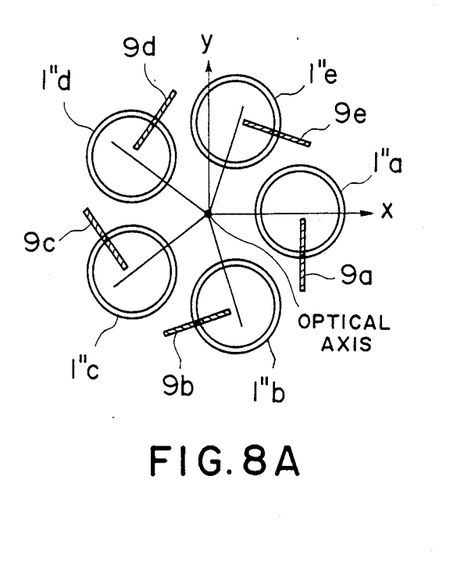
FIG. 8A is a relative view of sensors and cornea projection images.

FIG. 8A shows the arrangement of the sensors and illustrates the relative relation between the cornea projection images 1"a-1"e and the sensors 9a-9e. The sensor 9a is provided in parallel to the measurement diametral line direction (y direction), so as to intersect the projection image 1"a at a point toward the center of the projection image 1"a and so as to be orthogonal to a direction passing the center of the corresponding aperture stop and the optical axis (x direction). The other sensors 9b-9e are likewise provided in parallel to the corresponding measurement diametral line direction.

However, the positions at which the sensors are disposed are not restricted thereto but the sensors may be disposed at any particular positions.

Figure 8B:
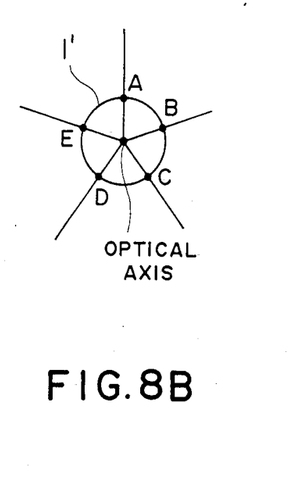
FIG. 8B illustrates the measured position of the corresponding image reflected by the cornea.

By the above-described position detection, the coordinates of five corresponding points A, B, C, D and E as shown in FIG. 8B are measured, whereby the elliptical shape of the image 1' reflected by the cornea is obtained.

To effect alignment and operating distance adjustment while effecting observation as shown in FIG. 1, the optical path is wavelength-divided by a dichroic mirror 6 and the front portion of the eye is illuminated by a light-emitting diode 12 so that the front portion of the eye can be imaged on an image pick-up tube 11 through a relay lens 10.

Figure 9:
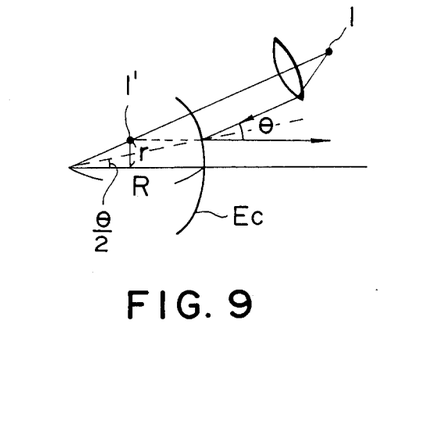
FIG. 9 illustrates the calculation of the radius of curvature of the cornea.

FIG. 9 illustrates how the radius of curvature R of the cornea is calculated from the elliptical shape of the image 1' reflected by the cornea.

Assuming that the angle formed between the illumination light ray and the measurement optical axis is $\theta$ and that the size of the image 1' reflected by the cornea is $\gamma$, the radius of curvature R of the cornea may be obtained from $$R = \frac{\gamma}{\sin\frac{\theta}{2}}.$$

If the present invention is used, the coordinates of the five points of intersection can be extracted even if the optical axis of the eye to be examined deviates from the measurement optical axis, and the shape of the image 1' reflected by the cornea can be calculated from this. As compared with the conventional maximum dimension measurement in three diametral line directions, it is not necessary to increase the alignment accuracy.

Figures 10, 10B:
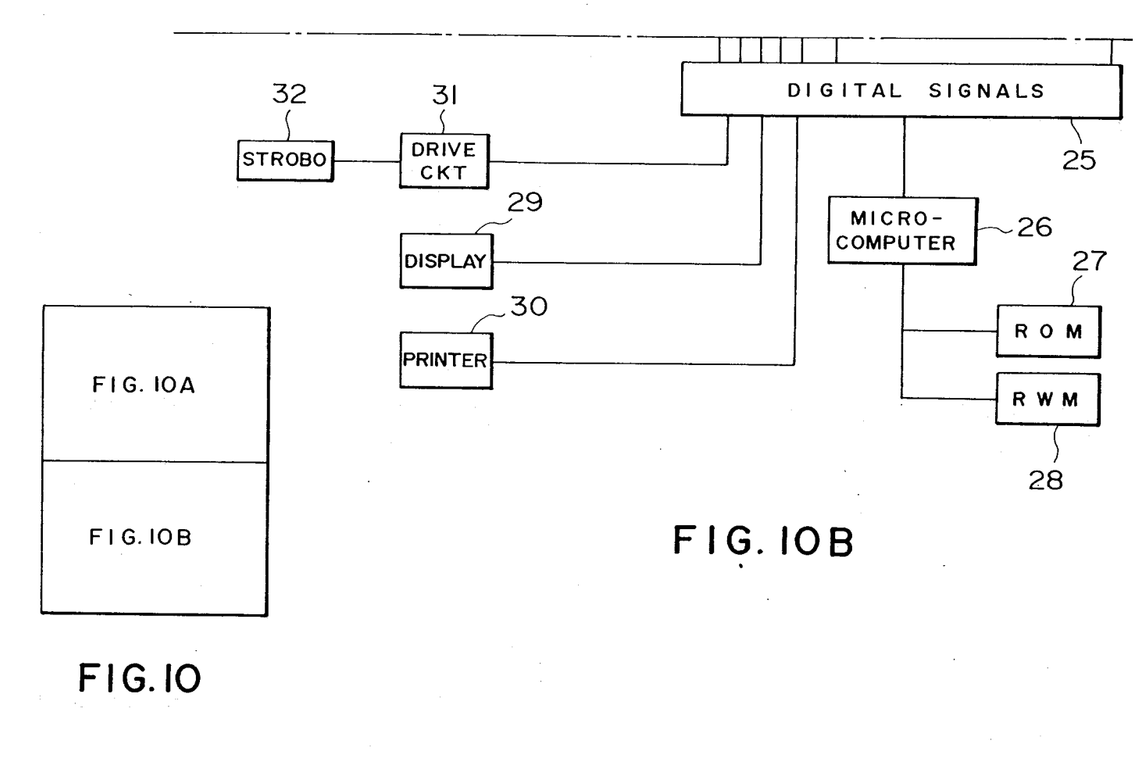
Figure 10A:
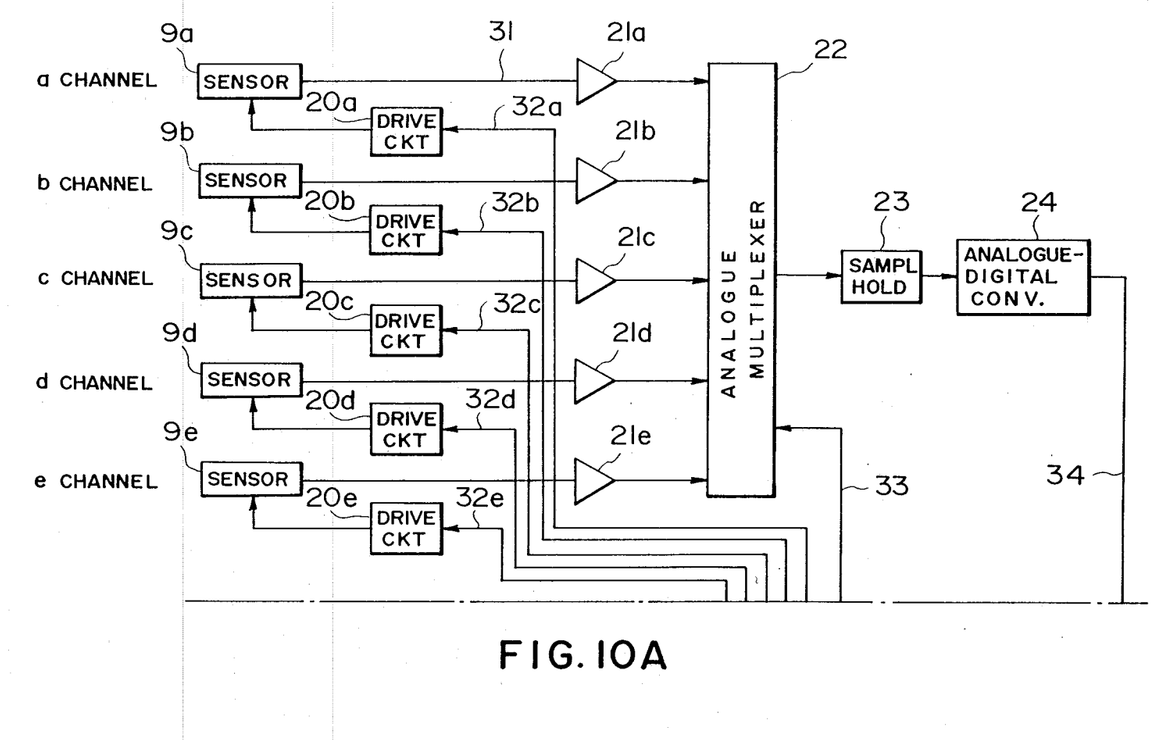

FIGS. 10A and 10B, assembled as shown in FIG. 10, constitute a block diagram showing an embodiment of the measurement signal processing circuit of the present apparatus.

The image 1' reflected by the cornea is projected separately onto the sensors 9a to 9e and the light and dark portions of the image are stored in the sensors.

In FIG. 10, channel a is first caused to select an analog multiplexer 22 by a channel selecting signal 33. A sensor read-out signal 32a is applied to a sensor driving circuit 20a, and in response thereto an analog signal 31 corresponding to the light and dark portions stored in the sensor 9a is taken out and amplified by an amplifier 21a, and is passed through the analog multiplexer 22 and is converted into a digital signal 25 by a sampling and holding circuit 23 and an analog-digital converter 24, and then is stored in a read-write memory 28. Likewise, the information of the sensors 9a to 9e is also analog-digital-converted by changing over a channel selecting signal 33 and sensor read-out signals 32b-32e in succession and this information is stored in the read-write memory 28. Designated by 27 is a read only memory. The position on the sensors 9a to 9e which is lightest is calculated by a microcomputer 26 on the basis of this information, whereby there are obtained five x, y coordinates having the optical axis of the image 1' reflected by the cornea in FIG. 8B as the origin.

Assuming that these coordinates are Xa to Xe and Ya to Ye, the unknown quantities a to e are obtained by substituting them into the general equation of a quadratic curve $ax^2 + bxy + cy^2 + dx + ey + 1 = 0$ and an equation of an elliptical curve is obtained to bring about the form of $x^2/a_o^2 + y^2/b_o^2 = 1$ by parallel movement and rotative movement of the coordinates axis.

From this, the major diameter and the minor diameter of the ellipse and the angle of rotation are obtained. An operation is then effected to calculate the radius of curvature, the refractive power, the degree of astigmatism and the astigmatic axis of the cornea, and the result is put out at a numerical display device 29 or a printer 30. Reference numeral 31 designates a strobo driving circuit, reference numeral 32 denotes a ring-like strobo, and reference numeral 34 designates a signal after the information from the sensors has been A/D-converted. The measurement time in the embodiment of FIG. 10 is equal to the time during which the image reflected by the cornea is stored in the sensors 9a to 9e. This is several milliseconds due to the light emission of the ring strobo 2. Thus, according to the present invention, the shape of the cornea can be measured within a short time.

Figure 11:
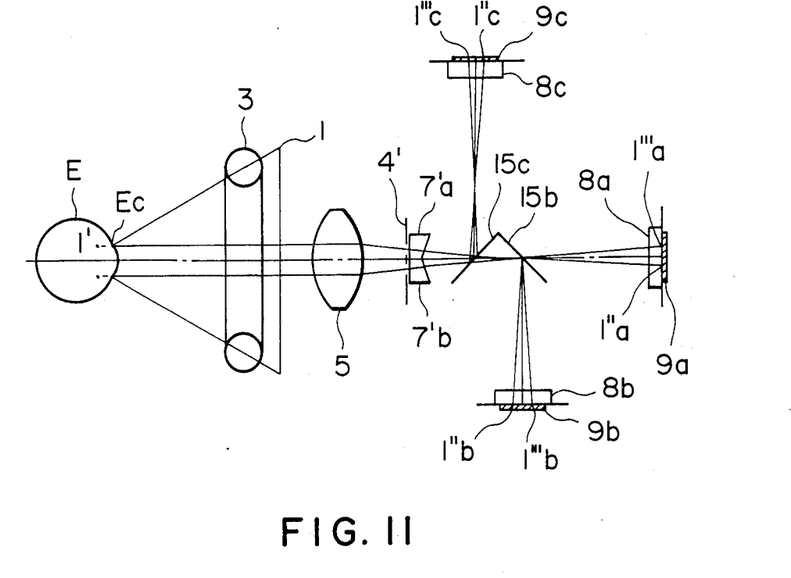
FIG. 11 shows a second embodiment of the apparatus according to the present invention.

FIG. 11 shows another embodiment which uses partially reflective mirrors to separate the image.

Figure 12:
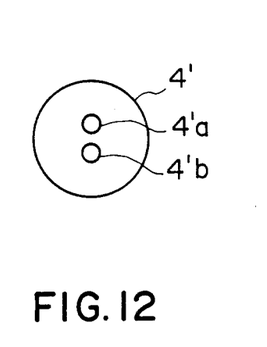
FIG. 12 shows a diaphragm plate.

The optical path is divided into three by partially reflective mirrors 15b and 15c. That is, the light beam from the image 1' reflected by the cornea passes through a projection lens 5, a diaghragm plate 4' and a prism 7', whereafter it travels to the sensor 9a through the mirrors 15c and 15b, to the sensor 9b through the mirror 15c and by being reflected by the mirror 15b, and to the sensor 9c by being reflected by the mirror 15c. The diaphragm plate 4' is provided with openings 4'a and 4'b in the direction of a diametral line as shown in FIG. 12, and the light beam is deflected in the direction of the same diametral line by prisms 7'a and 7'b to which correspond to the light beams passed through the respective openings.

Figure 13:
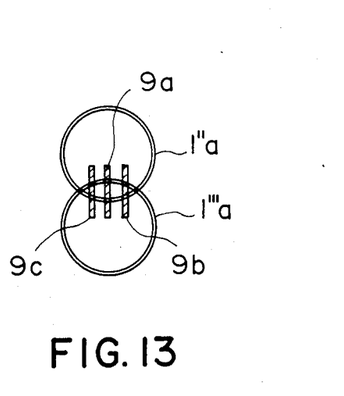
FIG. 13 is a view showing relative positions of sensors and cornea projection images.

The sensors 9a, 9b and 9c are provided parallel to one another as shown, for example, in FIG. 13 and extract five of six points of intersection detected by the separated image reflected by the cornea. Even if the optical axis of the eye to be examined and the measurement optical axis deviate from each other, the coordinates of five points of intersection can be extracted and, even if the alignment accuracy is low, measurement becomes possible. Calculation of the shape of the image 1' reflected by the cornea will now be described.

Figure 14A:
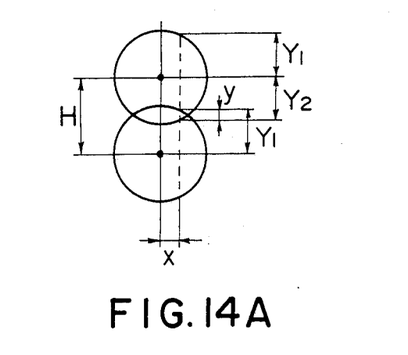
FIGS. 14A and 14B illustrate the calculation of an elliptical shape.

When the amount of deflection on the image plane by the prism 7' is H as shown in FIG. 14A, if the length y interposed between two images is measured, the length $Y_1 + Y_2$ in a direction parallel to a predetermined diametral line satisfies the following equation:

$$Y_1 + Y_2 = y + H$$

Figure 14B:
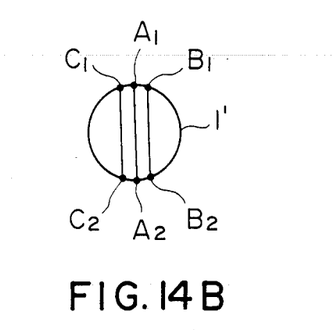

If the coordinates of the points A1, B1 and C1 shown in FIG. 14B are found from this, the coordinates of points A2, B2 and C2 can be found from the reading of y. The relative coordinates of A1, B1 and C1 can be read by the one-dimensional sensor. By extracting any five of these six points of intersection A1, B1, C1, A2, B2 and C2 and operating them, the afore-mentioned equation for the ellipse can be solved. The sensors 9a to 9e need not be provided in parallel to one another but may be set in any positional relation.

Figure 15:
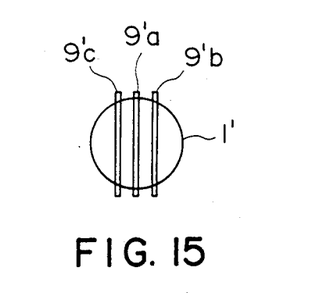
FIG. 15 shows a third embodiment of the apparatus according to the present invention.

Also, if the dimensions of the sensors can be selected to be large, as shown in FIG. 15, the image 1' reflected by the cornea can be directly detected without being separated by a prism and it is possible to extract five of the six points of intersection and measure the shape of the cornea.

In the present invention, the sixth point can be used to ascertain the accuracy. Also, the calculation of the elliptical shape can be accomplished not by electrical automatic operation but by naked eye observation.

While the present invention has been described with respect to a case where automatic detection is effected by one-dimensional sensors, it is of course possible to effect automatic detection by two-dimensional sensors and, even in a case where one-dimensional sensors are used, the number of sensors is not restricted.

Although the index projection system has been described as the transmitting type such as includes the annular cylindrical lens or the disc-like Fresnel cylindrical lens, it may also be of the reflection type using, for example, a concave mirror the cross-section of which in the direction of a diametral line is of a parabolic shape and, in this case, the ring-like light source is disposed at the focus position of parabola in the direction of each diametral line.

As described above, according to the present invention, accurate measurement of the shape of the cornea can be accomplished without enhancing the alignment accuracy in a plane perpendicular to the optical axis and without enhancing the positional accuracy in the direction of the optical axis. Further, the measurement can be accomplished within a short time, any measurement error resulting from movement of the eye to be examined can be prevented and measurement of the eyes of old men or children whose lines of vision are not stable becomes easy.

What we claim is:

1. A method for measuring the shape of the cornea of an eye, comprising the steps of:
    projecting a ring-like index onto the cornea of the eye by converting rays emitted from said index to parallel rays;
    detecting the position coordinates of at least five points of the image of said index reflected by the cornea;
    calculating a general formula of the elliptical shape of the image reflected by the cornea from the result of said detection; and
    obtaining the shape of the cornea from said calculation.

2. An apparatus for measuring the shape of the cornea of an eye, said apparatus comprising:
    a ring-like index;
    index projection means for projecting said ring-like index onto the cornea of the eye by converting rays emitted from said index to parallel rays;
    imaging means for forming the image of said index reflected by the cornea onto an imaging plane; and
    position detecting means provided on the imaging plane for detecting the position of the image formed on the imaging plane by said imaging means.

3. The apparatus according to claim 2, wherein said index projection means comprises a strobo light.

4. The apparatus according to claim 2, wherein said imaging means comprises a telecentric optical system.

5. The apparatus according to claim 4, wherein said index projection means comprises an annular cylindrical lens having a refractive power in the direction of diametral lines of the cornea and having no refractive power in a circumferential direction orthogonal to the diametral lines.

6. The apparatus according to claim 5, wherein said index projection means comprises a cylindrical lens having a Fresnel cross section.

7. The apparatus according to claim 2, wherein said position detecting means comprises at least three one-dimensional position detecting means.

8. The apparatus according to claim 2, wherein said position detecting means comprises two-dimensional position detecting means.

9. An apparatus for measuring the shape of the cornea of an eye, said apparatus comprising:
    a ring-like index;
    index projection means for projecting said ring-like index onto the cornea of the eye by converting rays emitted from said index to parallel rays;
    means for separating a light beam from the reflected image of said index reflected by the cornea;
    imaging means for forming the reflected image of said index reflected by the cornea, and the light beam of which has been separated by said separating means, onto an imaging plane; and
    position detecting means provided on the imaging plane for detecting the position of the image formed on the imaging plane by said imaging means.

10. The apparatus according to claim 9, wherein said imaging means comprises a telecentric optical system.

11. The apparatus according to claim 9, wherein said position detecting means comprises at least three one-dimensional position detecting means.

12. An apparatus for measuring the shape of the cornea of an eye, said apparatus comprising:
    a ring-like index;
    index projection means for projecting said ring-like index onto the cornea of the eye by converting rays emitted from said index to parallel rays;
    means for separating a light beam from the reflected image of said index reflected by the cornea into at least five light beams;
    imaging means for forming the reflected images of said index reflected by the cornea and from said at least five light beams separated by said separating means on an imaging plane; and
    at least five one-dimensional position detecting means provided on the imaging plane for detecting the position of the separated images formed on the imaging plane by said imaging means.

13. The apparatus according to claim 12, wherein said means for separating the light beam from the reflected image comprises diaphragm means for separating the light beam from the reflected image into at least five sub-light beams, and light beam deflecting means for deflecting the separated sub-light beams to corresponding one-dimensional position detecting means.

14. The apparatus according to claim 13, wherein said diaphragm means is formed with a plurality of openings and wherein the reflected light forming the reflected images from the cornea and passing through the central position of each opening of said diaphragm means is parallel to the measurement optical axis.

15. The apparatus according to claim 14, wherein said diaphragm means is provided at the focus position of said imaging means in the direction of the optical axis and the central position of each opening of said diaphragm means is displaced from the optical axis in a plane perpendicular to the optical axis.

16. The apparatus according to claim 15, wherein the detection direction of said one-dimensional position detecting means is orthogonal to a direction passing through the center of the corresponding opening of said diaphragm means and the optical axis.

17. The apparatus according to claim 16, wherein each said one-dimensional position detecting means is provided so as to intersect at about the center of the separated image.

18. The apparatus according to claim 12, further comprising means for condensing each of the separated light beams entering one said one-dimensional position detecting means in a direction orthogonal to the detection direction of said one-dimensional position detecting means.

19. The apparatus according to claim 12, wherein said index projection means comprises a strobo light.

20. The apparatus according to claim 12, wherein said one-dimensional position detecting means comprise CCDs.

* * * * *